(12) United States Patent
Katakowski et al.

(10) Patent No.: US 9,555,060 B2
(45) Date of Patent: Jan. 31, 2017

(54) METHODS, SYSTEMS, AND COMPOSITIONS FOR CELL-DERIVED/VESICLE-BASED MICRORNA DELIVERY

(71) Applicant: Henry Ford Health System, Detroit, MI (US)

(72) Inventors: Mark E. Katakowski, Ann Arbor, MI (US); Benjamin A. L. Buller, Detroit, MI (US); Michael Chopp, Southfield, MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 14/365,218

(22) PCT Filed: Dec. 13, 2012

(86) PCT No.: PCT/US2012/069419
§ 371 (c)(1),
(2) Date: Jun. 13, 2014

(87) PCT Pub. No.: WO2013/090523
PCT Pub. Date: Jun. 20, 2013

(65) Prior Publication Data
US 2015/0157666 A1    Jun. 11, 2015

Related U.S. Application Data

(60) Provisional application No. 61/570,081, filed on Dec. 13, 2011.

(51) Int. Cl.
| | | |
|---|---|---|
| *A61K 48/00* | (2006.01) | |
| *C07H 21/02* | (2006.01) | |
| *C07H 21/04* | (2006.01) | |
| *A61K 35/28* | (2015.01) | |
| *C12N 15/11* | (2006.01) | |
| *C12N 15/113* | (2010.01) | |
| *A61K 9/127* | (2006.01) | |

(52) U.S. Cl.
CPC .............. *A61K 35/28* (2013.01); *A61K 9/127* (2013.01); *C12N 15/111* (2013.01); *C12N 15/113* (2013.01); *C12N 2310/141* (2013.01); *C12N 2320/32* (2013.01); *C12N 2330/50* (2013.01)

(58) Field of Classification Search
CPC .............................. A61K 48/00; C12N 15/113
See application file for complete search history.

(56) References Cited

FOREIGN PATENT DOCUMENTS

| WO | WO 2007/126386 A1 * | 11/2007 | ......... C12N 2310/11 |
| WO | WO 2009/147519 A1 * | 12/2009 | ............. A61K 48/00 |

OTHER PUBLICATIONS

Okada (Title and abstract, J-Stage, Nov. 2010;130(11):1513-8).*
Roccaro Aldo M. et al: "Stroma-drived eosomes mediate oncogenesis in multiple myeloma," Blood, vol. 118, No. 21, Nov. 18, 2011 (Nov. 18, 2011, p. 286, XP002699283, 53rd Annual Meeting and Exposition of the American-Society-of-Hematology (ASH); San Diego CA, USA; Dec. 10-13, 2011 the whole document.
Katakowski Mark et al: "MiR-146b-5p supresses EGFR expression and reduces in vitro migration and invasion of glioma," Cancer Investigation, vol, 28, No. 10, Dec. 2010 (Dec. 2010), pp. 1024-1030, XP008163186, ISSN: 0735-7907, DOI: 10.3109/07357907.2010.512596 the whole document.
Katakowski Mark et al: "Exosomes from marrow stromal cells expressing miR-146b inhibit glioma growth," Cancer Letters, vol. 335, No. 1, Jul. 1, 2013 (Jul. 1, 2013), pp. 201-204, XP55067757, ISSN: 0304-3835, DOI: 10.1016/j.canlet.2013.02.019.
Baj-Krzyworzeka, Monika, et al: "Tumour-derived microvesicles carry several surface determinants and mRNA of tumor cells and transfer some of these determinants to monocytes," Cancer Immunology, Immunotherapy, vol. 55, issue 7, pp. 808-818.
Valadi, Hadi, et al: "Exosome-mediated transfer of mRNAs and microRNAs is a novel mechanism of genetic exchange between cells," Nature Cell Biology 9, (2007) pp. 654-659.
PCT/US2012/069419 International Search Report mailed on Nov. 7, 2013.

* cited by examiner

*Primary Examiner* — Amy Bowman
(74) *Attorney, Agent, or Firm* — Honigman Miller Schwartz and Cohn LLP; Fernando Alberdi; Jonathan P. O'Brien

(57) ABSTRACT

Some embodiments comprise methods, systems, and compositions to produce and/or administer modified exosomes or other vesicles containing one or more selected microRNAs, including but not limited to, miR-146b. Some embodiments also comprise the therapeutic administration and use of such modified exosomes and/or producer cells to treat mammalian injuries and diseases, including in human beings.

20 Claims, 5 Drawing Sheets

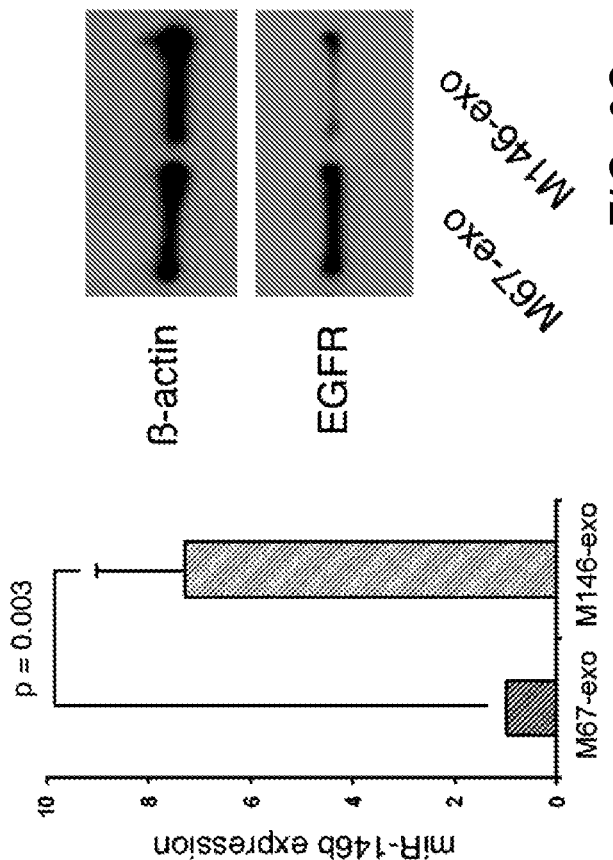
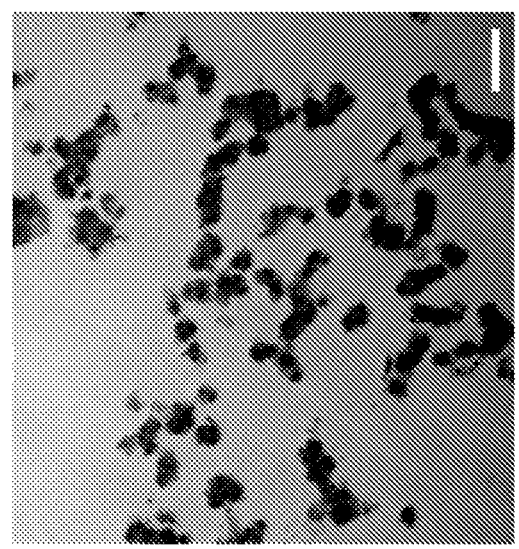
FIG. 6A
FIG. 6B
FIG. 6C

SEQUENCE LISTING

<160> NUMBER OF SEQ ID NOS: 4

<210> SEQ ID NO 1
<211> LENGTH: 4930
<212> TYPE: DNA
<213> ORGANISM: Artificial Sequence
<220> FEATURE:
<223> OTHER INFORMATION: Plasmid

<400> SEQUENCE: 1
tagttattaa tagtaatcaa ttacggggtc attagttcat agcccatata tggagttccg    60
cgttacataa cttacggtaa atggcccgcc tggctgaccg cccaacgacc cccgcccatt  120

```
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta caactccgc cccattgacg caaatgggcg gtaggcgtgt       540
acggtgggag gtctatataa gcagagctgg tttagtgaac cgtggatccc gtcgcttacc      600
gattcagaat ggttgatatc cgccattctg aatcggtaag cgacgaagct taataaagga     660
tcttttattt tcattggatc tgtgtgttgg ttttttgtgt gcggccgccc tcgactgtgc      720
cttctagaag acaatagcag gcatgctggg gatgcggtgg gctctatggc ttctgaggcg      780
gaaagaacca gctggggctc taggggtat ccccacgcgc cctgtagcgg cgcattaagc       840
gcggcgggtg tggtggttac gcgcagcgtg accgctacac ttgccagcgc cctagcgccc     900
gctcctttcg ctttcttccc ttcctttctc gccacgttcg ccggctttcc ccgtcaagct      960
ctaaatcggg ggctcccttt agggttccga tttagtgctt tacggcacct cgaccccaaa     1020
aaacttgatt agggtgatgg ttcacgtagt gggccatcgc cctgatagac ggttttttcgc    1080 cctttgacgt tggagtccac gttctttaat agtggactct tgttccaaac tggaacaaca    1140
ctcaacccta tctcggtcta ttcttttgat ttataaggga ttttgccgat ttcggcctat     1200
tggttaaaaa atgagctgat ttaacaaaaa tttaacgcga attaattctg tggaatgtgt     1260
gtcagttagg gtgtggaaag tccccaggct ccccagcagg cagaagtatg caaagcatgc     1320
atctcaatta gtcagcaacc aggtgtggaa agtccccagg ctccccagca ggcagaagta     1380
tgcaaagcat gcatctcaat tagtcagcaa ccatagtccc gcccctaact ccgcccatcc     1440
cgcccctaac tccgcccagt tccgcccatt ctccgcccca tggctgacta atttttttta     1500
tttatgcaga ggccgaggcc gcctctgcct ctgagctatt ccagaagtag tgaggaggct    1560 ttttggagg cctaggcttt tgcaaaaagc tcccgggatg accgagtaca agcccacggt      1620
gcgcctcgcc acccgcgacg acgtcccgcg ggccgtacgc accctcgccg ccgcgttcgc    1680
cgactacccc gccacgcgcc acaccgtcga cccggaccgc cacatcgagc gggtcaccga    1740
gctgcaagaa ctcttcctca cgcgcgtcgg gctcgacatc ggcaaggtgt gggtcgcgga    1800
cgacggcgcc gcggtggcgg tctggaccac gccggagagc gtcgaagcgg gggcggtgtt    1860
cgccgagatc ggcccgcgca tggccgagtt gagcggttcc cggctggccg cgcagcaaca    1920
gatggaaggc ctcctggcgc cgcaccggcc caaggagccc gcgtggttcc tggccaccgt    1980
cggcgtctcg cccgaccacc agggcaaggg tctgggcagc gccgtcgtgc tccccggagt    2040
ggaggcggcc gagcgcgccg gggtgcccgc cttcctggag acctccgcgc ccgcaacct    2100 ccccttctac gagcggctcg gcttcaccgt caccgccgac gtcgaggtgc ccgaaggacc    2160
gcgcacctgg tgcatgaccc gcaagcccgg tgcctgattc gaatgaccga ccaagcgacg    2220
cccaacctgc catcacgaga tttcgattcc accgccgcct tctatgaaag gttgggcttc    2280
ggaatcgttt tccgggacgc cggctggatg atcctccagc gcggggatct catgctggag    2340
ttcttcgccc accccaactt gtttattgca gcttataatg gttacaaata aagcaatagc    2400
atcacaaatt tcacaaataa agcatttttt tcactgcatt ctagttgtgg tttgtccaaa    2460
ctcatcaatg tatcttatca tgtctgtata ccgtcgacct ctagctagag cttggcgtaa    2520
```

```
tcatggtcat agctgtttcc tgtgtgaaat tgttatccgc tcacaattcc acacaacata    2580
cgagccggaa gcataaagtg taaagcctgg ggtgcctaat gagtgagcta actcacatta    2640
attgcgttgc gctcactgcc cgctttccag tcgggaaacc tgtcgtgcca gctgcattaa    2700
tgaatcggcc aacgcgcggg gagaggcggt ttgcgtattg ggcgctcttc cgcttcctcg    2760
ctcactgact cgctgcgctc ggtcgttcgg ctgcggcgag cggtatcagc tcactcaaag    2820
gcggtaatac ggttatccac agaatcaggg gataacgcag gaaagaacat gtgagcaaaa    2880
ggccagcaaa aggccaggaa ccgtaaaaag gccgcgttgc tggcgttttt ccataggctc    2940
cgcccccctg acgagcatca caaaaatcga cgctcaagtc agaggtggcg aaacccgaca    3000
ggactataaa gataccaggc gtttccccct ggaagctccc tcgtgcgctc tcctgttccg    3060
accctgccgc ttaccggata cctgtccgcc tttctccctt cgggaagcgt ggcgctttct    3120
catagctcac gctgtaggta tctcagttcg gtgtaggtcg ttcgctccaa gctgggctgt    3180
gtgcacgaac cccccgttca gcccgaccgc tgcgccttat ccggtaacta tcgtcttgag    3240
tccaacccgg taagacacga cttatcgcca ctggcagcag ccactggtaa caggattagc    3300
agagcgaggt atgtaggcgg tgctacagag ttcttgaagt ggtggcctaa ctacggctac    3360
actagaagaa cagtatttgg tatctgcgct ctgctgaagc cagttacctt cggaaaaaga    3420
gttggtagct cttgatccgg caaacaaacc accgctggta gcggtttttt tgtttgcaag    3480
cagcagatta cgcgcagaaa aaaaggatct caagaagatc ctttgatctt ttctacgggg    3540
tctgacgctc agtggaacga aaactcacgt taagggattt tggtcatgag attatcaaaa    3600
aggatcttca cctagatcct tttaaattaa aaatgaagtt ttaaatcaat ctaaagtata    3660
tatgagtaaa cttggtctga cagttaccaa tgcttaatca gtgaggcacc tatctcagcg    3720
atctgtctat ttcgttcatc catagttgcc tgactccccg tcgtgtagat aactacgata    3780
cgggagggct taccatctgg ccccagtgct gcaatgatac cgcgagaccc acgctcaccg    3840
gctccagatt tatcagcaat aaaccagcca gccggaaggg ccgagcgcag aagtggtcct    3900
gcaactttat ccgcctccat ccagtctatt aattgttgcc gggaagctag agtaagtagt    3960
tcgccagtta atagtttgcg caacgttgtt gccattgcta caggcatcgt ggtgtcacgc    4020
tcgtcgtttg gtatggcttc attcagctcc ggttcccaac gatcaaggcg agttacatga    4080
tcccccatgt tgtgcaaaaa agcggttagc tccttcggtc ctccgatcgt tgtcagaagt    4140
aagttggccg cagtgttatc actcatggtt atggcagcac tgcataattc tcttactgtc    4200
atgccatccg taagatgctt ttctgtgact ggtgagtact caaccaagtc attctgagaa    4260
tagtgtatgc ggcgaccgag ttgctcttgc ccggcgtcaa tacgggataa taccgcgcca    4320
catagcagaa ctttaaaagt gctcatcatt ggaaaacgtt cttcggggcg aaaactctca    4380
aggatcttac cgctgttgag atccagttcg atgtaaccca ctcgtgcacc caactgatct    4440
tcagcatctt ttactttcac cagcgtttct gggtgagcaa aaacaggaag caaaatgcc     4500 gcaaaaaagg gaataagggc gacacggaaa tgttgaatac tcatactctt cctttttcaa    4560
tattattgaa gcatttatca gggttattgt ctcatgagcg gatacatatt tgaatgtatt    4620
tagaaaaata aacaaatagg ggttccgcgc acatttcccc gaaaagtgcc acctgacgtc    4680
gacggatcgg gagatctccc gatcccctat ggtgcactct cagtacaatc tgctctgatg    4740
ccgcatagtt aagccagtat ctgctccctg cttgtgtgtt ggaggtcgct gagtagtgcg    4800
cgagcaaaat ttaagctaca acaaggcaag gcttgaccga caattgcatg aagaatctgc    4860
```

```
ttagggttag gcgttttgcg ctgcttcgcg atgtacgggc cagatatacg cgttgacatt    4920
gattattgac                                                            4930

<210> SEQ ID NO 2
<211> LENGTH: 72
<212> TYPE: DNA
<213> ORGANISM: Caenorhabditis elegans

<400> SEQUENCE: 2
ggatcctcac aacctcctag aaagagtaga ttgatatccg tctactcttt ctaggaggtt    60
gtgacgaagc tt                                                        72

<210> SEQ ID NO 3
<211> LENGTH: 5268
<212> TYPE: DNA
<213> ORGANISM: Artificial Sequence
<220> FEATURE:
<223> OTHER INFORMATION: Plasmid
<220> FEATURE:
<221> NAME/KEY: misc_feature
<222> LOCATION: (1307)..(1406)
<223> OTHER INFORMATION: n is a, c, g, t or u

<400> SEQUENCE: 3
cccaactttt aaaagaaaag gggggattgg ggggtacagt gcaggggaaa gaatagtaga    60
cataatagca acagacatac aaactaaaga attacaaaaa caaattacaa aattcaaaat   120
tttatcgatg cctccccgtc accaccccc ccaacccgcc ccgaccggag ctgagagtaa    180
ttcatacaaa aggactcgcc cctgccttgg ggaatcccag ggaccgtcgt taaactccca   240
ctaacgtaga acccagagat cgctgcgttc ccgccccctc acccgcccgc tctcgtcatc    300
actgaggtgg agaagagcat gcgtgaggct ccggtgcccg tcagtgggca gagcgcacat    360
cgcccacagt ccccgagaag ttgggggag gggtcggcaa ttgaaccggt gcctagagaa    420
ggtggcgcgg ggtaaactgg gaaagtgatg tcgtgtactg gctccgcctt tttcccgagg    480
gtgggggaga accgtatata agtgcagtag tcgccgtgaa cgttcttttt cgcaacgggt    540
ttgccgccag aacacaggta agtgccgtgt gtggttcccg cgggcctggc ctctttacgg    600
gttatggccc ttgcgtgcct tgaattactt ccacgcccct ggctgcagta cgtgattctt    660
gatcccgagc ttcggttgg aagtgggtgg gagagttcga ggccttgcgc ttaaggagcc    720
ccttcgcctc gtgcttgagt tgaggcctgg cctgggcgct ggggccgccg cgtgcgaatc    780
tggtggcacc ttcgcgcctg tctcgctgct ttcgataagt ctctagccat ttaaaatttt    840
tgatgatatc ctgcgacgct ttttttctgg caagatagtc ttgtaaatgc gggccaagat    900
ctgcacactg gtatttcggt ttttgggcc gcggcggcg acggggcccg tgcgtcccag    960
cgcacatgtt cggcgaggcg gggcctgcga gcgcggccac cgagaatcgg acgggggtag   1020
tctcaagctg gccggcctgc tctggtgcct ggcctcgcgc cgccgtgtat cgccccgccc   1080
tgggcggcaa ggctggcccg gtcggcacca gttgcgtgag cggaaagatg gccgcttccc   1140
ggccctgctg cagggagctc aaaatggagg acgcggcgct cgggagagcg ggcgggtgag   1200
tcacccacac aaaggaaaag gccctttccg tcctcagccg tcgcttcatg tgactccacg   1260
gagtaccggg cgccgtccag gcacctcgat tagttctcga ggatccnnnn nnnnnnnnn   1320 nnnnnnnnnn nnnnnnnnnn nnnnnnnnnn nnnnnnnnnn nnnnnnnnnn nnnnnnnnnn   1380
nnnnnnnnnn nnnnnnnnnn nnnnnngcta gctcgagctt ttggagtacg tcgtctttag   1440 gttggggga ggggttttat gcgatggagt ttccccacac tgagtgggtg gagactgaag   1500
```

```
ttaggccagc ttggcacttg atgtaattct ccttggaatt tgccctttt gagtttggat    1560 cttggttcat tctcaagcct cagacagtgg ttcaaagttt ttttcttcca tttcaggtgt    1620
cgtgaaaact accctctag agtcgagcta ccggtcgcca ccatggtgag caagggcgag    1680
gaggataaca tggccatcat caaggagttc atgcgcttca aggtgcacat ggagggctcc    1740
gtgaacggcc acgagttcga gatcgagggc gagggcgagg ccgcccta cgagggcacc    1800 cagaccgcca agctgaaggt gaccaagggt ggccccctgc ccttcgcctg ggacatcctg    1860
tcccctcagt tcatgtacgg ctccaaggcc tacgtgaagc accccgccga catccccgac    1920
tacttgaagc tgtccttccc cgagggcttc aagtgggagc gcgtgatgaa cttcgaggac    1980
ggcggcgtgg tgaccgtgac ccaggactcc tccctgcagg acggcgagtt catctacaag    2040
gtgaagctgc gcggcaccaa cttcccctcc gacggccccg taatgcagaa gaagaccatg    2100
ggctgggagg cctcctccga gcggatgtac cccgaggacg gcgccctgaa gggcgagatc    2160
aagcagaggc tgaagctgaa ggacggcggc cactacgacg ctgaggtcaa gaccacctac    2220
aaggccaaga gcccgtgca gctgcccggc gcctacaacg tcaacatcaa gttggacatc    2280
acctcccaca acgaggacta caccatcgtg aacagtacg aacgcgccga gggccgccac    2340
tccaccggcg gcatggacga gctgtacaag gacccaccgg tcgccaccat gaccgagtac    2400
aagcccacgt gcgcctcgc cacccgcgac gacgtcccca gggccgtacg caccctcgcc    2460
gccgcgttcg ccgactaccc cgccacgcgc cacaccgtcg atccggaccg ccacatcgag    2520
cgggtcaccg agctgcaaga actcttcctc acgcgcgtcg gctcgacat cggcaaggtg    2580 tgggtcgcgg acgacggcgc cgcggtggcg gtctggacca cgccggagag cgtcgaagcg    2640
ggggcggtgt cgccgagat cggcccgcgc atggccgagt tgagcggttc ccggctggcc    2700
gcgcagcaac agatggaagg cctcctggcg ccgcaccggc caaggagcc cgcgtggttc    2760 ctggccaccg tcggcgtctc gcccgaccac cagggcaagg gtctgggcag cgccgtcgtg    2820
ctccccggag tggaggcggc cgagcgcgcc ggggtgcccg ccttcctgga gacctccgcg    2880
ccccgcaacc tccccttcta cgagcggctc ggcttcaccg tcaccgccga cgtcgagtgc    2940
ccgaaggacc gcgcgacctg gtgcatgacc cgcaagcccg gtgcctgagc ggccgcaatc    3000
tagaccaaac ttgttattg cagcttataa tggttacaaa taaagcaata gcatcacaaa    3060
tttcacaaat aaagcatttt tttcactgca ttctagttgt ggtttgtcca aactcatcaa    3120
tgtatcttat catgtctgtg atcaggtacc aaagggcctc gtgatacgcc tatttttata    3180
ggttaatgtc atgataataa tggtttctta gacgtcaggt ggcactttc ggggaaatgt    3240 gcgcggaacc cctatttgtt tattttcta aatacattca aatatgtatc cgctcatgag    3300
acaataaccc tgataaatgc ttcaataata ttgaaaagg aagagtatga gtattcaaca    3360
tttccgtgtc gcccttattc cctttttgc ggcattttgc cttcctgttt tgctcaccc    3420 agaaacgctg gtgaaagtaa aagatgctga agatcagttg ggtgcacgag tgggttacat    3480
cgaactggat ctcaacagcg gtaagatcct tgagagttt cgccccgaag aacgttttcc    3540
aatgatgagc acttttaaag ttctgctatg tggcgcggta ttatcccgta ttgacgccgg    3600
gcaagagcaa ctcggtcgcc gcatacacta ttctcagaat gacttggttg agtactcacc    3660
agtcacagaa aagcatctta cggatggcat gacagtaaga gaattatgca gtgctgccat    3720
aaccatgagt gataacactg cggccaactt acttctgaca acgatcggag gaccgaagga    3780
gctaaccgct tttttgcaca acatgggga tcatgtaact cgccttgatc gttgggaacc    3840
```

```
ggagctgaat gaagccatac caaacgacga gcgtgacacc acgatgcctg tagcaatggc    3900
aacaacgttg cgcaaactat taactggcga actacttact ctagcttccc ggcaacaatt    3960
aatagactgg atggaggcgg ataaagttgc aggaccactt ctgcgctcgg cccttccggc    4020
tggctggttt attgctgata aatctggagc cggtgagcgt gggtctcgcg gtatcattgc    4080
agcactgggg ccagatggta agccctcccg tatcgtagtt atctacacga cggggagtca    4140
ggcaactatg gatgaacgaa atagacagat cgctgagata ggtgcctcac tgattaagca    4200
ttggtaactg tcagaccaag tttactcata tatactttag attgatttaa aacttcattt    4260
ttaattaaaa agatctaggt gaagatcctt tttgataatc tcatgaccaa aatcccttaa    4320
cgtgagtttt cgttccactg agcgtcagac cccgtagaaa agatcaaagg atcttcttga    4380
gatccttttt ttctgcgcgt aatctgctgc ttgcaaacaa aaaaaccacc gctaccagcg    4440
gtggtttgtt tgccggatca agagctacca actctttttc cgaaggtaac tggcttcagc    4500
agagcgcaga taccaaatac tgttcttcta gtgtagccgt agttaggcca ccacttcaag    4560
aactctgtag caccgcctac atacctcgct ctgctaatcc tgttaccagt ggctgctgcc    4620
agtggcgata gtcgtgtct taccgggttg gactcaagac gatagttacc ggataaggcg    4680
cagcggtcgg gctgaacggg gggttcgtgc acacagccca gcttggagcg aacgacctac    4740
accgaactga gatacctaca gcgtgagcta tgagaaagcg ccacgcttcc cgaagggaga    4800
aaggcggaca ggtatccggt aagcggcagg gtcggaacag gagagcgcac gagggagctt    4860 ccaggggga  acgcctggta tctttatagt cctgtcgggt ttcgccacct ctgacttgag    4920
cgtcgatttt tgtgatgctc gtcaggggg  cggagcctat ggaaaaacgc cagcaacgcg    4980 gccttttttac ggttcctggc cttttgctgg ccttttgctc acatgttctt tcctgcgtta    5040
tcccctgatt ctgtggataa ccgtattacc gcctttgagt gagctgatac cgctcgccgc    5100
agccgaacga ccgagcgcag cgagtcagtg agcgaggaag cggaagagcg cccaatacgc    5160
aaaccgcctc tccccgcgcg ttggccgatt cattaatgca gctggcacga caggtttccc    5220
gactggaaag cgggcagtga gcgcaacgca attaatgtga gttagctc                5268
```

<210> SEQ ID NO 4
<211> LENGTH: 293
<212> TYPE: DNA
<213> ORGANISM: Homo sapiens

<400> SEQUENCE: 4

```
tcgaggatcc tgacccatcc tgggcctcaa cttactcatc ctgggaacgg gagacgattc      60
acagaagaaa gcatgcaaga gcagcgtcca ggctgaaaga actttggcca cctggcactg     120
agaactgaat tccataggct gtgagctcta gcaatgccct gtggactcag ttctggtgcc     180
cggcagtgct acaacatcaa tgccaaggcc gtggggcagc tgatggtttg ggctcccaac     240
ttcccagcca ggtgcttctg caggcccaca tcttgcccac tgggctagct cga            293
```

METHODS, SYSTEMS, AND COMPOSITIONS FOR CELL-DERIVED/VESICLE-BASED MICRORNA DELIVERY

CROSS-REFERENCE TO RELATED APPLICATIONS

This application is a U.S. National Phase Application of PCT/US2012/069419 filed Dec. 13, 2012, which claims the benefit of U.S. Provisional Patent Application Ser. No. 61/570,081 filed Dec. 13, 2011, entitled "Methods, Systems, and Compositions for Cell-derived Vesicle-based MicroRNA Delivery," each of which is hereby incorporated by reference in its entirety.

TECHNICAL FIELD

Without limitation, some embodiments of the invention comprise methods, systems, and compositions relating to microRNAs and the use of same in the research, diagnosis, and treatment of injury or disease.

BACKGROUND

Despite advances in diagnostics, chemotherapeutics, and surgical techniques, the prognosis for certain types of cancers, including but not limited to, brain cancers like glioblastoma multiforme ("GBM"), remains poor.

MicroRNAs ("miRNAs" or "miRs") can regulate gene expression in cells and might be used for therapeutic benefit. As nonlimiting examples, miRNAs can be used to inhibit tumor progression, or to promote tissue healing. Epidermal growth factor receptor ("EGFR") and miR-146b expression have been shown to be inversely correlated in GBMs. However, many EGFR inhibitors have largely failed to induce GBM regression clinically, even where the relationship between genotype and drug response is observed in other cancers. Moreover, GBMs display a variety of genetic aberrations. Thus, a need remains for therapeutic treatments for many cancers, including but not limited to, GBM.

One difficulty that must be overcome for effective miRNA therapy is efficient delivery of the therapeutic miRNAs into the targeted cells, tissues, or organs. A predominant technical challenge in developing a miRNA-based therapy is getting target cells to efficiently absorb and incorporate significant amounts of miRNA.

SUMMARY

The following examples of some embodiments are provided without limiting the invention to only those embodiments described herein and without disclaiming any embodiments or subject matter.

Some embodiments provide methods, systems, and/or compositions using miRNAs which are effectively targeted to, absorbed by, and/or incorporated in cells, tissues, or organs for therapeutic treatments. Some embodiments comprise methods, systems, and/or compositions to produce and/or administer modified exosomes or other vesicles containing one or more selected miRNAs, including but not limited to, miR-146b. In some embodiments, without limitation, miRNA-encoding plasmids are transfected into producer cells, including but not limited to, multipotent mesenchymal stromal cells ("MSCs"). Exosomes containing the transfected miRNAs are harvested from those cells and are used for administration to a subject suffering from injury or illness. Additionally or alternatively, producer cells having miRNA derived from the modified exosomes may be harvested and administered to the subject. Some embodiments comprise the therapeutic administration and use of such miRNAs, modified exosomes, and/or producer cells to treat mammalian injuries and diseases, including in human beings.

BRIEF DESCRIPTION OF THE DRAWINGS

Some embodiments will now be described, by way of example only and without disclaimer of other embodiments, with reference to the accompanying drawings, in which:

FIG. 6 is images and graphs showing an electron micrograph of MSC exosomes isolated from MSC culture medium, real-time PCR detection of miR-146b expression in M67-exo and M146-exo, and a Western blot for β-actin and EGFR protein expression in 9L cells treated with M67-exo and M146-exo.

DETAILED DESCRIPTION

Figure 1:
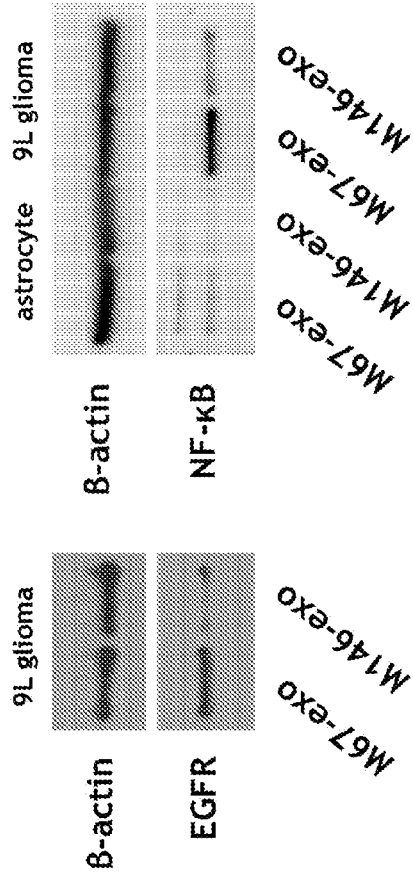
FIG. 1 is a data representation and images showing that exosomes from MSCs transfected with a miR-146b expression plasmid reduce EGFR and NF-κB when administered to cultures of 9L glioma cells.

Without limitation to only those embodiments expressly disclosed herein and without disclaiming any embodiments or subject matter, some embodiments comprise a miRNA delivery system whereby miRNA expression is modified in target exosome-producing cells (as one nonlimiting example, MSCs), and exosomes or other vesicles, miRNAs from those cells, and/or those cells themselves, are used as delivery vehicles to deliver therapeutic miRNA(s) into cells, tissue, or organs. Some embodiments comprise the therapeutic administration and use of such induced cells to treat mammalian injuries and diseases, including but not limited to, nervous system injuries or diseases that may otherwise result in decreased cell or system function. In some embodiments, such induction of differentiated MSCs, and/or the resulting cells, may be used to treat cell, tissue, or organ damage in a patient by administering to said patient a therapeutically effective amount of a miRNA of interest, or of differentiated MSCs induced by such miRNAs.

A pressing problem in treatment with miRNA is getting target cells to efficiently absorb and incorporate the miRNA. Some embodiments will effectively deliver therapeutic miRNAs to tissue or other locations within a subject for treatment. For example, certain embodiments could be used to produce custom exosomes that carry one or more species of anti-tumor miRNAs that could be administered to a cancer patient. Alternately, certain embodiments could be used to produce custom exosomes that carry one or more species of neuro-restorative miRNAs that could be administered to a stroke patient. Some embodiments comprise a customizable miRNA delivery system that could be used to treat multiple pathologies in whose treatment miRNA therapy would be useful.

MiRNAs can regulate gene expression in cells, and can be used for therapeutic benefit. For example, miRNAs can be used to inhibit tumor progression, or to promote tissue healing. One difficulty that must be overcome for effective miRNA therapy is efficient delivery of the miRNA(s) to the affected cell, tissues or organs.

Some embodiments comprise the packaging of exosomes with one or more species of miRNA, and as the miRNA can be endogenous to the producing cell, or foreign, or artificially designed (as only one example, by original DNA plasmid(s) design), they comprise a versatile method of miRNA delivery. For example, whereas many nucleotide delivery vehicles such as liposomes or nanoparticles require preloading or binding the vehicle with the nucleotide, certain embodiments use the producer cells to create the miRNA and to load the exosome.

Introducing foreign particles into a patient can result in an immune response. In certain embodiments, if cells such as MSCs are used, it is possible to use the patient's own MSCs as producer cells; therefore, it is likely that immune rejection of the delivery vehicles could be circumvented or reduced.

Without limitation, some embodiments comprise ongoing production of miRNA-bearing exosomes, and also enable transplantation of miRNA-bearing exosome producing cells. Once transfected, producer cells could create or continue to produce custom miRNA-bearing exosomes and miRNAs for an extended period of time. The miRNA may comprise the entire sequence of the miRNA, or it may comprise any subfragment or variant thereof which retains the targeted activity of the entire sequence. This creation or production could provide certain advantages, including but not limited to: 1) exosomes could be harvested at many time points and delivered to the patient over many days or weeks, and 2) the producer cells themselves might be transplanted into the tissue to be treated to produce custom miRNA-bearing exosomes and miRNAs on site.

We have discovered that miRNAs that are introduced into MSCs, and certain other cell types, are subsequently released from the cells in exosomes. As a nonlimiting example, when we transfected MSCs with a DNA plasmid that encoded the *C. elegans* miRNA cel-miR-67, we found an abundance of cel-miR-67 miRNA in the exosomes released from these MSCs. As exosomes can be incorporated in other cells, we have invented, in some embodiments, a miRNA production and delivery system whereby miRNA expression is modified in target exosome-producing cells (as one nonlimiting example, MSCs), and exosomes from those cells, and/or the cells themselves, are used as delivery vehicles to take therapeutic miRNA(s) into cells, tissue, or organs.

In some embodiments, we transfected producer cells (MSCs, 9L glioma cells and HEK cells) with DNA plasmids that are designed to encode for miRNAs. In some embodiments, we used plasmids that encoded for cel-miR-67 (a control miRNA not found in mammalian cells), and miR-146b (a miRNA that we previously found had anti-tumor effects). We harvested exosomes produced from these cells (after 1 day, 2 days and 3 days), and using RT-PCR, we detected cel-miR-67 only in exosomes from cells that were transfected with the cel-miR-67 plasmid. Furthermore, we detected highly elevated levels (up to 160× control) of miR-146b in the exosomes that were transfected with the miR-146b plasmid. Based on our other work, treating glioma cells with cel-miR-67 would have no effect upon cell viability, whereas treating glioma cells with miR-146b would reduce cell viability and reduce tumor cell invasion. Deletions on chromosome 10 are the most frequent chromosomal alteration observed in GBMs, with approximately 80% of cases exhibiting loss of heterozygosity. Human miR-146b is located on chromosome 10 within 10q24-26, a region most frequently lost in GBM. We found that U87-MG, U251 and cells, and HFH66 primary human glioblastoma cells, express significantly less miR-146b than normal cortical human astrocytes. EGFR gene amplification occurs in approximately 40% of all GBMs and increased EGFR expression correlates with glioma invasiveness and malignancy. The EGFR signaling network has been a target for anti-tumor therapy, with significant effort focused on inhibiting the receptor using antibodies, tyrosine kinase inhibitors, or vaccines.

In our work, we treated 9L gliosarcoma cells with exosomes from cel-miR-67 plasmid-transfected cells and miR-146b plasmid-transfected cells, as well as exosomes from non-transfected cells. Using MTT we found that glioma cell viability was significantly reduced when treated with exosomes from miR-146b plasmid transfected cells compared to all controls. Therefore, using a miR-146b plasmid and producer cells, we effectively and efficiently administered miR-146b to tumor cells, eliciting a significant anti-tumor effect.

MiRNAs inhibit translation of their target mRNAs. MiR-146b can inhibit production of certain tumor promoting proteins, among them, EGFR, NF-κB, IRAK1 and TRAF6. Using Western blot, we have found that exosomes from cells transfected with miR-146b plasmid significantly reduced EGFR, NF-κB, IRAK-1, and TRAF6 expression in glioma cells compared to cells treated with control exosomes or exosomes from cel-miR-67 plasmid transfected cells. Other proteins that are targets of miR-146b in other systems were unaffected, such as MMP16, indicating that the effect we observed was specific. FIG. 1 shows protein expression in glioma cells and astrocytes after exposure to MSC exosomes. As indicated, miR-146b exosomes ("M146-exo") reduced EGFR and NF-κB protein expression in 9L cells compared to cel-miR-67 exosomes ("M67-exo"). NF-κB M146-exo also slightly reduced NF-κB protein in primary cortical rat astrocytes. These results show that miR-146b packaged in exosomes could significantly inhibit its targeted proteins in treated tumor cells but not non-tumor astrocytes.

Some embodiments comprise a novel and versatile miRNA delivery system which can be applied in a wide range of diseases or injuries. Using some embodiments clinically, anti-tumor miRNAs could be packaged in exosomes, and these exosomes could be administered to the subject. The ability to efficiently package one or more species of miRNAs of some embodiments results in a versatile miRNA delivery system. Thus, depending upon the miRNAs that are packaged, a wide range of diseases or injuries could be treated with modified exosomes comprising some embodiments.

Furthermore, as described herein, producer cells could be administered to a targeted location in a subject, resulting in local sustained production of custom miRNA bearing exosomes, and/or the therapeutic release of selected miRNAs from the producer cells themselves.

Certain embodiments comprise features which include, but are not limited to: 1) an effective method of miRNA delivery as cell derived vesicles are easily incorporated into cells, 2) production of cell derived vesicles (as one nonlimiting example, exosomes) that can contain one or more species of miRNA, and these can be endogenously occurring, or custom designed miRNAs, 3) as any miRNA(s) can be packaged, production of miRNA—bearing exosomes for treatment of many different diseases, 4) use of exosome-producing cells for an ongoing supply of ex vivo miRNA-bearing exosomes, and/or transplantation in vivo to locally produce miRNA-bearing exosomes, 5) use of multiple cell types to produce miRNA-bearing exosomes, 6) use of modified cells and/or exosomes designed to specifically target tissues of therapeutic interest, and 7) avoidance or mitigation of adverse effects, as exosomes are naturally occurring and thus custom miRNA bearing exosomes will likely have few adverse effects when administered.

Some embodiments may comprise the production and/or administration of other similarly modified, cell-derived membrane vesicles in addition to or concurrently with modified exosomes.

Figure 2:
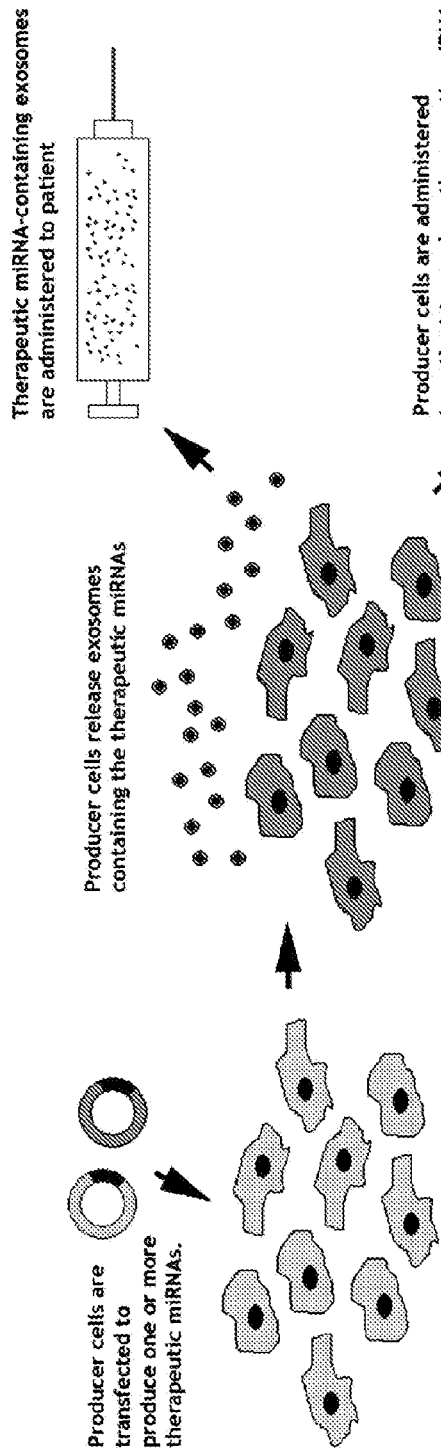
FIG. 2 shows an overview of an exosome-based therapeutic miRNA delivery system.

Certain embodiments comprise methods, systems, and/or compositions to deliver therapeutic miRNA molecules into tissue of patients. As illustrated in FIG. 2, some embodiments comprise methods and/or systems with one or more of the following steps: 1) MiRNAs that have been determined to be therapeutic are expressed in exosome producing cells, 2) the producing cells begin to release exosomes that contain the introduced therapeutic miRNAs, and 3) therapeutic miRNA-containing exosomes are harvested and administered to the patient, and/or producing cells are administered to the patient to release therapeutic miRNA-containing exosomes after administration.

Some embodiments comprise the packaging of exosomes with one or more species of miRNA at high concentrations, and these miRNAs are delivered into tissue in therapeutic doses. Packaged miRNAs can be those that are endogenous to the producing cells, but are forced to express at higher levels, or may be artificially designed miRNAs, introduced to suit the therapeutic need. Also, a combination of miRNAs can be packaged within the same exosomes.

EXAMPLES

The following examples of some embodiments are provided without limiting the invention to only those embodiments described herein and without disclaiming any embodiments.

Example 1

Figure 3:
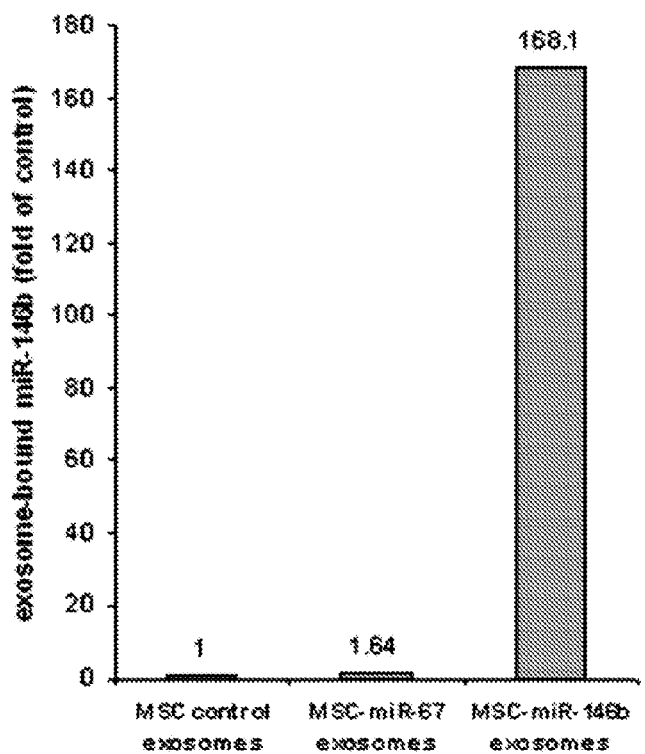
FIG. 3 is a data representation showing that exosomes from MSCs transfected with a miR-146b expression plasmid release exosomes that contain significantly higher levels of miR-146b.

We have found that miRNAs that are introduced into MSCs or other cells are subsequently packaged in exosomes in abundance, and released from the cells. These exosomes containing introduced miRNAs can then be isolated from the culture medium. For example, when we transfected MSCs with a DNA plasmid that encoded miRNA cel-miR-67, we found an abundance of cel-miR-67 miRNA in the exosomes released from these MSCs. MiRNA cel-miR-67 is not naturally produced by mammalian MSCs. Therefore in some embodiments, one can package non-native miRNAs into exosomes, which means that some embodiments might be used to design small miRNA-like sequences that are customized to target any gene of interest. We also found unexpectedly that when MSC cells were transfected with rno-miR-146b, a miRNA native to mammalian MSCs, exosomes from miR-146b-transfected MSCs contained significantly higher levels of miR-146b compared to control (FIG. 3). We detected miR-146b levels to be relatively higher in exosomes from miR-146b producing cells compared to exosomes from naive cells, than the miR-146b levels in the cell bodies of the respective groups. Furthermore, the levels of miR-146b detected in MSC exosomes from miR-146b producing cells was consistently and unexpectedly increased to levels several fold higher than that of cel-miR-67 detected in exosomes from cel-miR-67 producing cells, even when normalized for naive levels of miR-146b in MSC exosomes. These data indicate that miR-146b is preferentially packaged into exosomes by the producer cells. As per above, exosomes can also be collected from certain other cell types, such as 9L, HEK, astrocytes, or oligodendrocytes. However, we found these certain other cell types lack the production capacity of MSCs, and as such, when transfected in accordance with some embodiments, MSCs are a novel and highly efficient producer cell. In addition, we found that miR-146b expression did not compromise production of exosomes by MSCs or significantly alter the viability of the MSCs, a key feature, as some anti-tumor miRNAs can suppress metabolic processes in cells. As exosomes can be incorporated in other cells, in some embodiments, we have developed the use of MSC exosomes as a delivery vehicle for therapeutic miRNAs.

Example 2

A current problem for treatment with therapeutic miRNA is getting the target cells to efficiently absorb and incorporate the miRNA. Some embodiments use exosomes that are easily absorbed from cells such as MSCs. We then package therapeutic miRNA or a combination of therapeutic miRNAs into MSC exosomes, and employ the exosomes as the delivery vehicle. For example, some embodiments could be used to produce custom exosomes that carry one or more species of anti-tumor miRNAs that could be administered to the cancer patient. Alternately, some embodiments could be used to produce custom exosomes that carry neuro-restorative miRNAs to be administered to a patient suffering from a neurological disease such as Alzheimer's disease, or stroke. Some embodiments comprise a customizable miRNA delivery system that could be used to treat multiple pathologies in which treatment with miRNA therapy would be useful.

Figure 4:
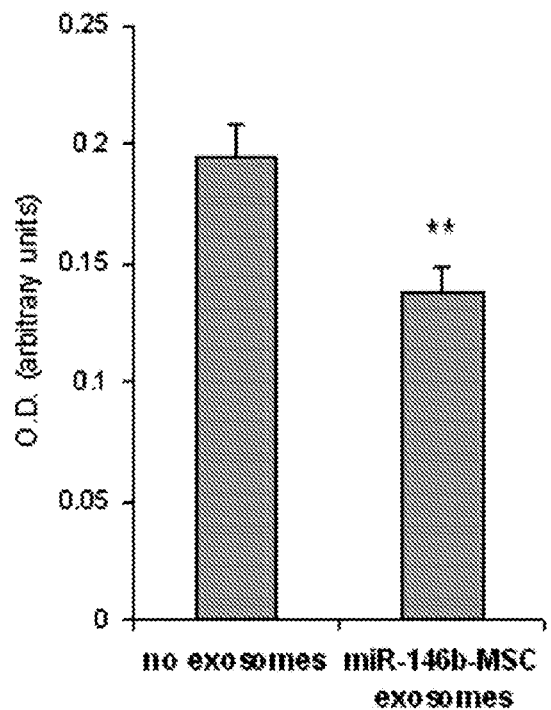
FIG. 4 is a data representation showing that exosomes from MSCs transfected with a miR-146b expression plasmid release exosomes that decrease viability of 9L gliosarcoma tumor cells.

We have packaged the anti-tumor miRNA miR-146b in MSC exosomes and treated 9L gliosarcoma cells with these exosomes in vitro. Using the MTT cell viability assay, we found that 9L gliosarcoma cell viability was significantly reduced when treated with miR-146b-containing MSC exosomes compared to control (FIG. 4, showing that exosomes from MSCs transfected with a miR-146b expression plasmid release exosomes that decrease cell viability of 9L gliosarcoma tumor cells.). Therefore, using a miR-146b plasmid and producer cells to package miR-146b in MSC exosomes, we effectively and efficiently administered miR-146b to tumor cells, eliciting a significant anti-tumor effect. To determine whether MSC exosomes carrying miR-146b deliver the miRNA into tumor cells, we exposed 9L cells to miR-146b-containing MSC exosomes (M146-exo) or cel-miR-67-containing exosomes (M67-exo) in vitro. After 24 hours treatment, miR-146b detected in M146-exo-treated 9L cells was 8.5±0.4 times higher compared to M67-exo-treated cells, whereas cel-miR-67 was detected in M67-exo-treated 9L cells, but not detected M146-exo-treated cells. This indicated that MSC exosomes can deliver plasmid-expressed miRNAs into tumor cells.

Example 3

Figure 5:
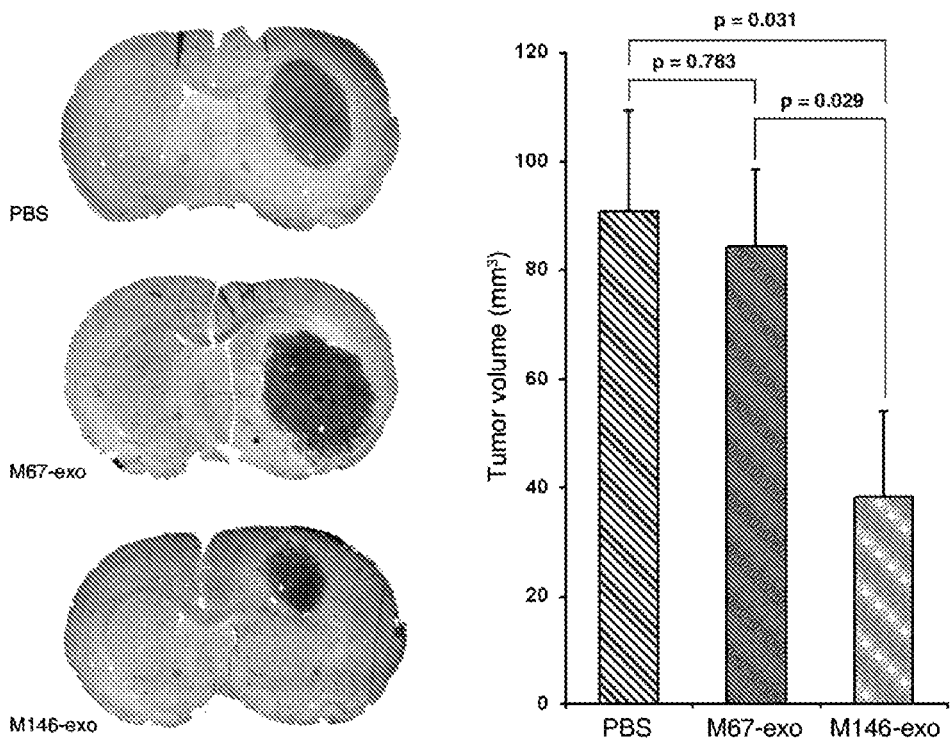
FIG. 5 is a data representation and images showing that exosomes from MSCs transfected with a miR-146b expression plasmid reduce tumor growth when administered to rats bearing 9L gliosarcoma tumors.

To determine whether an anti-tumor miRNA packaged in MSC exosomes would reduce tumor growth in vivo, we treated rats bearing 9L gliosarcoma brain tumors with these MSC exosomes package with miR-146b via intra-tumor administration. 24 Fischer rats were implanted with 9L gliosarcoma. After 5 days, cel-miR-67-containing exosomes from cel-miR-67-transfected MSCs (control), or miR-146b-containing exosomes from miR-146b-transfected MSCs, or saline treatment were administered by intra-tumor injection (n=8 per treatment group). 10 days after tumor implantation, animals were sacrificed and tumor volume was calculated. As shown in FIG. 5, treatment with miR-146b-containing MSC exosomes significantly reduced tumor growth in rats bearing 9L gliosarcoma tumors compared to cel-miR-67-containing MSC exosome control (cel-miR-67 does not have binding sites in rat mRNA). (FIG. 5 legend: PBS (vehicle only), M146-exo or cel-miR-67 exosomes ("M67-exo") was administered via intra-tumor injection 5 days after tumor implant. Animals were sacrificed at 10 days post-implant (n=8 per group). Bars are standard deviation.)

Example 4

Exosomes are generally 30-150 nm vesicles secreted by a wide range of mammalian cells that can contain miRNA. To determine whether MSC exosomes could be used as a vehicle for delivery of anti-tumor miRNAs, we transfected MSCs with a miR-146b expression plasmid, and harvested exosomes released by the MSCs. Intra-tumor injection of exosomes derived from miR-146-expressing MSCs significantly reduced glioma xenograft growth in a rat model of primary brain tumor.

Aberrant gene expression is a mechanism of miRNA dysfunction in cancer, including in GBMs, and miRNAs are differentially expressed in GBM relative to normal tissue. Human mir-146b is located on chromosome 10 within 10q24-26 (10q24.32, 104186259-104186331+), a region lost in a majority of these tumors. miR-146b reduces glioma cell motility and invasion, and EGFR mRNA is a binding-target for miR-146b silencing. EGFR gene amplification occurs in approximately 40% of all GBMs and increased EGFR correlates with glioma invasiveness and malignancy. We employed a 9L xenograft model of primary brain tumor to determine whether miR-146b could function as an anti-glioma miRNA in vivo.

Materials and Methods:
Tumor Implantation.
Male Fischer rats (250-275 g) were used. A 2 mm diameter craniotomy was made on the right hemisphere anterior to the coronal suture. Using a Hamilton syringe, tumor cells were injected 3.5 mm deep, 3.0 mm to the right and 1.0 mm anterior of the bregma. Rats were implanted with $2.5 \times 10^5$ 9L cells (5 µl PBS) over a 15-minute interval. The craniotomy was covered with Horsley's bone wax, and the incision was closed with 4-0 silk suture (Ethicon). Animals were weighed at tumor implantation, treatment, and prior to sacrifice. No statistical difference in weights was detected between treatment groups. Rats were sacrificed 10 days after implantation under anesthesia with i.p. administration of ketamine (100 mg/kg) and xylazine (10 mg/kg). Animals were perfused with 10% formalin following vascular washout with 0.9% saline. Brains were removed, fixed and cut into 2 mm thick blocks which were embedded in paraffin. Sections were stained with hematoxylin and eosin. To measure tumor volume, in each coronal section, the area of the tumor was measured using MCID software (InterFocus Imaging) by tracing the demarcation of the tumor, and the section volume was determined by multiplying the traced area by the section thickness.

Plasmids and MSC Transfection.
Cel-miR-67 and hsa-miR-146b expression plasmids (GenScript) were used. The plasmid used with respect to cel-miR-67 was the pRNA-CMV3.1/Puro plasmid, SEQ ID NO: 1; see also http://www.genscript.com/vector/SD1233-pRNA_CM3_1_Puro.html, which is hereby incorporated by reference. The inserted cel-miR-67 sequence comprised SEQ ID NO: 2. The plasmid used with respect to has-miR-146b was the pEP-miR plasmid, SEQ ID NO: 3; see also http://www.cellbiolabs.com/sites/default/files/MIR-146B.pdf, which is hereby incorporated by reference. The inserted has-miR-146b sequence comprised SEQ ID NO: 4. MSC transfection was performed using electroporation. $2 \times 10^6$ MSCs were suspended in 150 µl of Ingenio Electroporation Solution (Minis) with 2 µg of plasmid DNA. Program A-33 was used for electroporation in an Amaxa Nucleofector Device. Transfected cells were resuspended in 10 ml complete culture medium, centrifuged, and then plated for exosome production.

Exosome Preparation and Harvest.
$2 \times 10^6$ MSCs were seeded in 10 ml Dulbecco's Modified Eagle Medium supplemented with 20% Fetal Bovine Serum. After 48 hours, exosomes were isolated from the MSC medium using ExoQuick-TC (System Biosciences, CA). Exosome pellets were resuspended in sterile PBS at a total protein concentration of 10 µg/µl. Exosome suspensions were placed on ice and administered to animals within 6 hours following harvest. Exosomes visualized by electron microscopy were fixed in glutaraldehyde (5 µg/µl) for 30 minutes.

Exosome Treatment.
For treatment, 5 µl of the M67-exo or M146-exo suspension was injected in each animal via intra-tumor injection at 5 days after tumor implantation. Using a Hamilton syringe, exosome suspension or PBS vehicle was injected at the same coordinates as the tumor implant, over a 5-minute interval. Real-time PCR was used to determine relative cel-miR-67 expression and miR-146b expression in M67-exo and M146-exo used for treatment. MiR-146b was 7.3±1.7 fold higher in M146-exo compared to M67-exo. Cel-miR-67 was not detected in M146-exo, but was detected with a CT value of 33.2±2.3 in M67-exo.

Real-Time PCR.
To analyze miRNA expression, MSC cells, 9L cells or MSC exosomes were lysed in Qiazol reagent and total RNA was isolated using the miRNeasy Mini kit (Qiagen). Reverse transcription was performed with the miRNA Reverse Transcription Kit (Applied Biosystems), and cDNA was amplified with TaqMan miRNA assays (Applied Biosystems), which are specific for mature miRNA sequences. 40 amplification cycles were performed. The 2-ΔΔCT method was used to determine relative miRNA expression. If a CT was not reached in 40 amplification cycles, the measured miRNA was considered to be undetected.

Western Blot.
$2 \times 10^5$ 9L cells were seeded in a 6-well plate and cultured overnight. M67-exo or M146-exo (50 µg total protein) in 5 µl PBS was added to the culture medium. 24 hours later 9L cells were lysed and Western blot was used to detect EGFR and β-actin (Santa Cruz Biotechnology). Protein concentration was quantified using a BCA protein assay kit (Pierce). SuperSignal West Pico Chemiluminescent Substrate (Pierce) and Kodak X-omat film (Kodak) exposure were used for visualization.

Statistical Analysis.

Data are shown as mean±s.e.m. P-values were calculated using one-way ANOVA or Student's t test. A p-value of 0.05 or less was considered statistically significant.

Results:

To determine whether MSCs package miR-146b into secreted exosomes, we transfected MSCs from rats with a plasmid encoding for miR-146b, or for cel-miR-67, which has no known mRNA binding targets in rat. 48 hours after transfection, exosomes were isolated from the medium, and miR-146b and cel-miR-67 were measured in MSCs and extra-cellular exosomes. FIG. 6A shows exosomes from MSCs transfected with miR-146b or cel-miR-67 expression plasmids. (FIG. 6A: Electron micrograph of MSC exosomes isolated from MSC culture medium, Scalebar=500 nm.) miR-146b was 7.1±3.7 fold higher in MSCs and 7.3±1.7 fold higher in MSC exosomes after miR-146b expression plasmid transfection, compared to miR-146 levels in cel-miR-67 plasmid transfected MSCs and their exosomes, respectively (FIG. 6B: real-time PCR detection of miR-146b expression in M67-exo and M146-exo (n=7). Data are mean±s.e.m.; comparison is two-tailed t-test.). Cel-miR-67 was not detected in miR-146b plasmid transfected MSCs or their exosomes (M146-exo), but was detected in cel-miR-67 plasmid transfected MSCs and their exosomes (M67-exo). These data demonstrate that plasmid-expressed miRNA is efficiently packaged into MSC exosomes by endogenous mechanisms.

To determine whether MSC exosomes carrying miR-146b deliver the miRNA into tumor cells, we exposed 9L cells to M146-exo or M67-exo in vitro. After 24 hours, miR-146b detected in M146-exo-treated 9L cells was 8.5±0.4 times higher compared to M67-exo-treated cells, whereas cel-miR-67 was detected in M67-exo-treated 9L cells, but not detected M146-exo-treated cells. Thus, MSC exosomes can deliver plasmid-expressed miRNAs into tumor cells in vitro. To determine whether M146-exo could alter target protein expression in tumor cells, we exposed 9L cells to M146-exo in vitro, and after 24 hours, EGFR protein levels were lower in M146-exo-treated 9L cells compared to M67-exo-treated 9L cells (FIG. 6C: Western blot for β-actin and EGFR protein expression in 9L cells treated with M67-exo and M146-exo.) These findings indicated to us that miR-146b, delivered via MSC exosomes, is functionally active in the acceptor tumor cells.

Figure 7A:
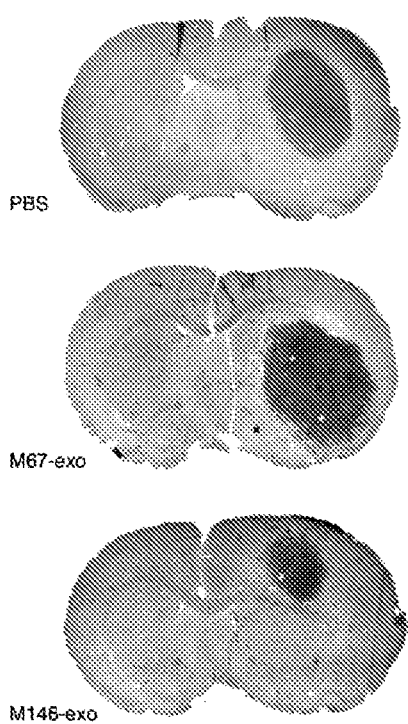
FIG. 7 is images of representative H&E-stained coronal sections from sacrificed rats after tumor implantation and a graph of volumetric measurement of 9L xenograft tumors.
Figure 7B:
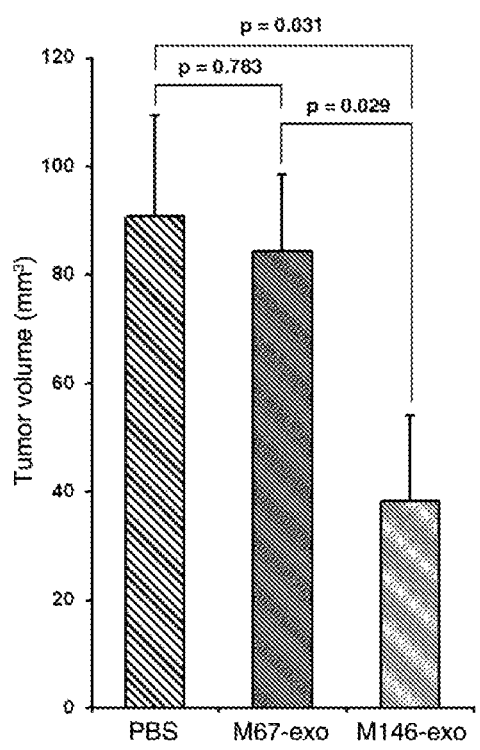

Finally, to determine whether M146-exo had an anti-tumor effect in vivo, we administered M146-exo or M67-exo (50 μg total protein in 5 μl volume) to Fischer rats bearing 9L gliosarcoma. We found that one intra-tumor injection of M146-exo 5 days after intracranial tumor xenograft implantation lead to a significant reduction in tumor volume at 10 days post-implant compared M67-exo or vehicle treated control (FIG. 7—A: Representative H&E-stained coronal sections from rats sacrificed 10 days after tumor implantation; B: Volumetric measurement of 9L xenograft tumors 10 days after tumor implant, and 5 days after PBS, M67-exo, or M146-exo treatment (n=8 per group). ANOVA: p=0.042. Data are mean±s.e.m. Post hoc multiple comparisons are two-tailed t-tests.). These data indicated to us that M146-exo elicits an anti-tumor effect in the rat brain.

Here, one intra-tumor injection of 50 μg M146-exo significantly reduced glioma xenograft growth in rat brain. Our findings indicate to us that export of specific therapeutic miRNA into MSC exosomes represents a new treatment strategy for at least malignant glioma.

As discussed herein, some embodiments comprise a novel treatment whereby therapeutic miRNA that is produced in MSCs and loaded into extra-cellular exosomes by endogenous mechanisms, is used to treat tumor.

Interest is growing in using exosomes as biological delivery vehicles. Exosomes are taken up by acceptor cells, whereby cellular processes can be altered. There is some evidence that exosomes do not elicit acute immune rejection, and as they are non-viable, they do not risk tumor formation. Furthermore, exosomes can be manufactured at scale in culture, possibly using autologous cells, and exosome-producing cells could incorporate multiple therapeutic miRNAs, enabling personalized treatment. Our work indicates that miRNA packaged into MSC exosomes are incorporated by tumor cells in culture. For in vivo treatment, we delivered exosomes directly by intra-tumor injection. There are indications that functional miRNAs are transferred between glioma cells, suggesting that therapeutic miRNAs may distribute throughout the tumor.

In some embodiments, without limitation or disclaimer, we employed MSCs as producer cells. However, other cell types may be employed as well to package miRNAs into exosomes. Once transfected, producer cells can create custom miRNA-bearing exosomes for an extended period of time. Thus, exosomes could be harvested at multiple time points and delivered to the patient over several days or weeks, or the producer cells themselves might be transplanted into the tissue to be treated to produce custom miRNA-bearing exosomes on site. Furthermore, the producer cells could be harvested from the patient's own bone marrow or other organs in order to limit any potential immune complications.

According to some embodiments useful in a clinical setting, therapeutic miRNAs could be packaged in exosomes, and these exosomes could be administered to the patient. Thus, depending upon the miRNAs that are packaged, a wide range of diseases could be treated with these custom exosomes.

According to some embodiments useful in a clinical setting, therapeutic miRNAs could be packaged in exosomes, and these exosomes could be frozen and stored for future administration to the patient. Thus, depending upon disease state, the patient's cells could be used to produce custom exosomes to be administered at a later time point.

In some embodiments, miRNAs are introduced into the MSCs (or other producer cells) to package the miRNAs in exosomes. However, the introduction of the miRNAs into the MSCs may alter the MSCs themselves, and importantly, the nature of the exosomes they produce. Thus, the resulting modification of the exosomes (and their other components) may have therapeutic effect in addition to the packaged miRNAs. MSCs (or other producer cells) can be transfected with miRNAs with the intent to modify the exosomes that are released.

Thus, without limitation and without disclaimer of subject matter, some embodiments comprise novel exosomes containing one or more selected miRNAs and/or producer cells containing same (collectively "modified exosome/producer cell administration") to prevent, control, or alleviate mammalian illness or injury through the selective application of such miRNAs. In accordance with some embodiments, without limitation, one may inhibit such illness or injury through modified exosome/producer cell administration for a finite interval of time, thereby limiting the development or course of such illness or injury.

In accordance with some embodiments, there is a high likelihood that the duration of therapy comprising modified exosome/producer cell administration would be relatively brief and with a high probability of success. Prophylactic modified exosome/producer cell administration of some embodiments may greatly reduce the incidence of damage associated with many forms of illness or injury.

Any appropriate routes of modified exosome/producer cell administration known to those of ordinary skill in the art may comprise some embodiments.

Modified exosomes/producer cells of some embodiments would be administered and dosed in accordance with good medical practice, taking into account the clinical condition of the individual patient, the site and method of administration, scheduling of administration, patient age, sex, body weight and other factors known to medical practitioners. The "pharmaceutically effective amount" for purposes herein is thus determined by such considerations as are known in the art. The amount must be effective to achieve improvement, including but not limited to, decreased damage or injury, or improvement or elimination of symptoms and other indicators as are selected as appropriate measures by those skilled in the art.

In accordance with some embodiments, modified exosomes/producer cells can be administered in various ways. They can be administered alone or as an active ingredient in combination with pharmaceutically acceptable carriers, diluents, adjuvants and vehicles. The modified exosomes/producer cells can be administered orally, subcutaneously or parenterally including intravenous, intraarterial, intramuscular, intraperitoneal, and intranasal administration as well as intrathecal and infusion techniques, or by local administration or direct inoculation to the site of disease or pathological condition. Implants of the modified exosomes/producer cells may also be useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active components of some embodiments. In some embodiments, modified exosomes/producer cells may be altered by use of antibodies to cell surface proteins or ligands of known receptors to specifically target tissues of interest.

Since the use of modified exosomes/producer cells administration in accordance with some embodiments specifically targets the evolution, expression, or course of associated pathologies, it is expected that the timing and duration of treatment in humans may approximate those established for animal models in some cases. Similarly, the doses established for achieving desired effects using such compounds in animal models, or for other clinical applications, might be expected to be applicable in this context as well. It is noted that humans are treated generally longer than the experimental animals exemplified herein which treatment has a length proportional to the length of the disease process and drug effectiveness. The doses may be single doses or multiple doses over periods of time. The treatment generally has a length proportional to the length of the disease process and drug effectiveness and the patient species being treated.

When administering the modified exosomes/producer cells of some embodiments parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When necessary, proper fluidity can be maintained, for example, by the use of a coating such as lecithin, by the maintenance of the required size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for such modified exosome/producer cell compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to some embodiments, however, any vehicle, diluent, or additive used would have to be compatible with the modified exosomes/producer cells.

Sterile injectable solutions can be prepared by incorporating modified exosomes/producer cells utilized in practicing the some embodiments in the required amount of the appropriate solvent with various of the other ingredients, as desired.

A pharmacological formulation of some embodiments may be administered to the patient in an injectable formulation containing any compatible carrier, such as various vehicle, adjuvants, additives, and diluents; or the inhibitor(s) utilized in some embodiments may be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In some embodiments, without limitation, the modified exosomes/producer cells may be administered initially by intravenous injection to bring blood levels to a suitable level. The patient's levels are then maintained by an oral dosage form, although other forms of administration, dependent upon the patient's condition and as indicated above, can be used. The quantity to be administered and timing of administration may vary for the patient being treated.

Additionally, in some embodiments, without limitation, modified exosomes/producer cells may be administered in situ to bring internal levels to a suitable level. The patient's levels are then maintained as appropriate in accordance with good medical practice by appropriate forms of administration, dependent upon the patient's condition. The quantity to be administered and timing of administration may vary for the patient being treated.

While the some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. It is intended that the following claims define the scope of the invention and that the method and apparatus within the scope of these claims and their equivalents be covered thereby. This description of the some embodiments should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

SEQUENCES

SEQ ID NO: 1-
TAGTTATTAATAGTAATCAATTACGGGGTCATTAGTTCATAGCCCATATATGGAGTTCCG
CGTTACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACGTCA
ATGGGTGGAGTATTTACGGTAAACTGCCCACTTGGCAGTACATCAAGTGTATCATATGCC
AAGTACGCCCCCTATTGACGTCAATGACGGTAAATGGCCCGCCTGGCATTATGCCCAGTA
CATGACCTTATGGGACTTTCCTACTTGGCAGTACATCTACGTATTAGTCATCGCTATTAC
CATGGTGATGCGGTTTTGGCAGTACATCAATGGGCGTGGATAGCGGTTTGACTCACGGGG
ATTTCCAAGTCTCCACCCCATTGACGTCAATGGGAGTTTGTTTTGGCACCAAAATCAACG
GGACTTTCCAAAATGTCGTAACAACTCCGCCCATTGACGCAAATGGGCGGTAGGCGTGT
ACGGTGGGAGGTCTATATAAGCAGAGCTGGTTTAGTGAACCGTGGATCCCGTCGCTTACC
GATTCAGAATGGTTGATATCCGCCATTCTGAATCGGTAAGCGACGAAGCTTAATAAAGGA
TCTTTTATTTTCATTGGATCTGTGTGTTGGTTTTTTGTGTGCGGCCGCCCTCGACTGTGC
CTTCTAGAAGACAATAGCAGGCATGCTGGGGATGCGGTGGGCTCTATGGCTTCTGAGGCG
GAAAGAACCAGCTGGGGCTCTAGGGGGTATCCCCACGCGCCCTGTAGCGGCGCATTAAGC
GCGGCGGGTGTGGTGGTTACGCGCAGCGTGACCGCTACACTTGCCAGCGCCCTAGCGCCC
GCTCCTTTCGCTTTCTTCCCTTCCTTTCTCGCCACGTTCGCCGGCTTTCCCCGTCAAGCT
CTAAATCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGGAACAACA
CTCAACCCTATCTCGGTCTATTCTTTTGATTTATAAGGGATTTTGCCGATTTCGGCCTAT
TGGTTAAAAAATGAGCTGATTTAACAAAAATTTAACGCGAATTAATTCTGTGGAATGTGT
GTCAGTTAGGGTGTGGAAAGTCCCCAGGCTCCCCAGCAGGCAGAAGTATGCAAAGCATGC
ATCTCAATTAGTCAGCAACCAGGTGTGGAAAGTCCCCAGGCTCCCCAGCAGGCAGAAGTA
TGCAAAGCATGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTTTTTTTA
TTTATGCAGAGGCCGAGGCCGCCTCTGCCTCTGAGCTATTCCAGAAGTAGTGAGGAGGCT
TTTTTGGAGGCCTAGGCTTTTGCAAAAAGCTCCCGGGATGACCGAGTACAAGCCCACGGT
GCGCCTCGCCACCCGCGACGACGTCCCGCGGGCCGTACGCACCCTCGCCGCCGCGTTCGC
CGACTACCCCGCCACGCGCCACACCGTCGACCCGGACCGCCACATCGAGCGGGTCACCGA
GCTGCAAGAACTCTTCCTCACGCGCGTCGGGCTCGACATCGGCAAGGTGTGGGTCGCGGA
CGACGGCGCCGCGGTGGCGGTCTGGACCACGCCGGAGAGCGTCGAAGCGGGGGCGGTGTT
CGCCGAGATCGGCCCGCGCATGGCCGAGTTGAGCGGTTCCCGGCTGGCCGCGCAGCAACA
GATGGAAGGCCTCCTGGCGCCGCACCGGCCCAAGGAGCCCGCGTGGTTCCTGGCCACCGT
CGGCGTCTGCCCGACCACCAGGGCAAGGGTCTGGGCAGCGCCGTCGTGCTCCCCGGAGT
GGAGGCGGCCGAGCGCGCCGGGGTGCCCGCCTTCCTGGAGACCTCCGCGCCCCGCAACCT
CCCCTTCTACGAGCGGCTCGGCTTCACCGTCACCGCCGACGTCGAGGTGCCCGAAGGACC
GCGCACCTGGTGCATGACCCGCAAGCCCGGTGCCTGATTCGAATGACCGACCAAGCGACG
CCCAACCTGCCATCACGAGATTTCGATTCCACCGCCGCCTTCTATGAAAGGTTGGGCTTC
GGAATCGTTTTCCGGGACGCCGGCTGGATGATCCTCCAGCGCGGGGATCTCATGCTGGAG
TTCTTCGCCCCACCCCAACTTGTTTATTGCAGCTTATAATGGTTACAAATAAAGCAATAGC
ATCACAAATTTCACAAATAAAGCATTTTTTTCACTGCATTCTAGTTGTGGTTTGTCCAAA
CTCATCAATGTATCTTATCATGTCTGTATACCGTCGACCTCTAGCTAGAGCTTGGCGTAA
TCATGGTCATAGCTGTTTCCTGTGTGAAATTGTTATCCGCTCACAATTCCACACAACATA
CGAGCCGGAAGCATAAAGTGTAAAGCCTGGGGTGCCTAATGAGTGAGCTAACTCACATTA
ATTGCGTTGCGCTCACTGCCCGCTTTCCAGTCGGGAAACCTGTCGTGCCAGCTGCATTAA
TGAATCGGCCAACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATCAGCTCACTCAAAG
GCGGTAATACGGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTTCCATAGGCTC
CGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGGATTAGC
AGAGCGAGGTATGTAGGCGGTGCTACAGAGTTCTTGAAGTGGTGGCCTAACTACGGCTAC
ACTAGAAGAACAGTATTTGGTATCTGCGCTCTGCTGAAGCCAGTTACCTTCGGAAAAAGA
GTTGGTAGCTCTTGATCCGGCAAACAAACCACCGCTGGTAGCGGTTTTTTTGTTTGCAAG
CAGCAGATTACGCGCAGAAAAAAAGGATCTCAAGAAGATCCTTTGATCTTTTCTACGGGG
TCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCG
ATCTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGTGGTGTCACGC
TCGTCGTTTGGTATGGCTTCATTCAGCTCCGGTTCCCAACGATCAAGGCGAGTTACATGA

SEQUENCES

TCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCT
TCAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCAA
TATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGACGTC
GACGGATCGGGAGATCTCCCGATCCCCTATGGTGCACTCTCAGTACAATCTGCTCTGATG
CCGCATAGTTAAGCCAGTATCTGCTCCCTGCTTGTGTGTTGGAGGTCGCTGAGTAGTGCG
CGAGCAAATTTAAGCTACAACAAGGCAAGGCTTGACCGACAATTGCATGAAGAATCTGC
TTAGGGTTAGGCGTTTTGCGCTGCTTCGCGATGTACGGGCCAGATATACGCGTTGACATT
GATTATTGAC

SEQ ID NO: 2-
GGATCCTCACAACCTCCTAGAAAGAGTAGATTGATATCCGTCTACTCTTTCTAGGAGGTT
GTGACGAAGCTT

SEQ ID NO: 3-
```
   1 cccaactttt aaaagaaaag gggggattgg ggggtacagt gcaggggaaa
     gaatagtaga
  61 cataatagca acagacatac aaactaaaga attacaaaaa caaattacaa
     aattcaaaat
 121 tttatcgatg cctccccgtc accaccccc ccaacccgcc ccgaccggag
     ctgagagtaa
 181 ttcatacaaa aggactcgcc cctgccttgg ggaatcccag ggaccgtcgt
     taaactccca
 241 ctaacgtaga acccagagat cgctgcgttc ccgcccctc acccgcccgc
     tctcgtcatc
 301 actgaggtgg agaagagcat gcgtgaggct ccggtgcccg tcagtgggca
     gagcgcacat
 361 cgcccacagt ccccgagaag ttgggggag gggtcggcaa ttgaaccggt
     gcctagagaa
 421 ggtggcgcgg ggtaaactgg gaaagtgatg tcgtgtactg gctccgcctt
     tttcccgagg
 481 gtgggggaga accgtatata agtgcagtag tcgccgtgaa cgttcttttt
     cgcaacgggt
 541 ttgccgccag aacacaggta agtgccgtgt gtggttcccg cgggcctggc
     ctctttacgg
 601 gttatggccc ttgcgtgcct tgaattactt ccacgcccct ggctgcagta
     cgtgattctt
 661 gatcccgagc ttcgggttgg aagtgggtgg gagagttcga ggccttgcgc
     ttaaggagcc
 721 ccttcgcctc gtgcttgagt tgaggcctgg cctgggcgct ggggccgccg
     cgtgcgaatc
 781 tggtggcacc ttcgcgcctg tctcgctgct ttcgataagt ctctagccat
     ttaaaatttt
 841 tgatgatatc ctgcgacgct tttttctgg caagatagtc ttgtaaatgc
     gggccaagat
 901 ctgcacactg gtatttcggt ttttggggcc gcgggcggcg acggggcccg
     tgcgtcccag
 961 cgcacatgtt cggcgaggcg gggcctgcga gcgcggccac cgagaatcgg
     acggggtag
1021 tctcaagctg gccggcctgc tctggtgcct ggcctcgcgc cgccgtgtat
     cgccccgccc
1081 tgggcggcaa ggctggcccg gtcggcacca gttgcgtgag cggaaagatg
     gccgcttccc
1141 ggccctgctg cagggagctc aaaatggagg acgcggcgct cgggagagcg
     ggcgggtgag
1201 tcacccacac aaaggaaaag ggcctttccg tcctcagccg tcgcttcatg
     tgactccacg
1261 gagtaccggg cgccgtccag gcacctcgat tagttctcga ggatccnnnn
     nnnnnnnnnn
1321 nnnnnnnnnn nnnnnnnnnn nnnnnnnnnn nnnnnnnnnn nnnnnnnnnn
     nnnnnnnnnn
1381 nnnnnnnnnn nnnnnnnnnn nnnnnngcta gctcgagctt ttggagtacg
     tcgtctttag
1441 gttgggggga ggggttttat gcgatggagt ttccccacac tgagtgggtg
     gagactgaag
1501 ttaggccagc ttggcacttg atgtaattct ccttggaatt tgcccttttt
     gagtttggat
1561 cttggttcat tctcaagcct cagacagtgg ttcaaagttt ttttcttcca
     tttcaggtgt
1621 cgtgaaaact accctctag agtcgagcta ccggtcgcca ccatggtgag
     caagggcgag
```

-continued

| SEQUENCES |
|---|

```
1681 gaggataaca tggccatcat caaggagttc atgcgcttca aggtgcacat
     ggagggctcc
1741 gtgaacggcc acgagttcga gatcgagggc gagggcgagg ccgcccccta
     cgagggcacc
1801 cagaccgcca agctgaaggt gaccaagggt ggccccctgc ccttcgcctg
     ggacatcctg
1861 tcccctcagt tcatgtacgg ctccaaggcc tacgtgaagc accccgccga
     catccccgac
1921 tacttgaagc tgtccttccc cgagggcttc aagtgggagc gcgtgatgaa
     cttcgaggac
1981 ggcggcgtgg tgaccgtgac ccaggactcc tccctgcagg acggcgagtt
     catctacaag
2041 gtgaagctgc gcggcaccaa cttcccctcc gacggccccg taatgcagaa
     gaagaccatg
2101 ggctgggagg cctcctccga gcggatgtac cccgaggacg gcgccctgaa
     gggcgagatc
2161 aagcagaggc tgaagctgaa ggacggcggc cactacgacg ctgaggtcaa
     gaccacctac
2221 aaggccaaga gcccgtgca gctgcccggc gcctacaacg tcaacatcaa
     gttggacatc
2281 acctcccaca acgaggacta caccatcgtg aacagtacg aacgcgccga
     gggccgccac
2341 tccaccggcg gcatggacga gctgtacaag gacccaccgg tcgccaccat
     gaccgagtac
2401 aagcccacgg tgcgcctcgc caccccgcgac gacgtcccca gggccgtacg
     caccctcgcc
2461 gccgcgttcg ccgactaccc cgccacgcgc cacaccgtcg atccggaccg
     ccacatcgag
2521 cgggtcaccg agctgcaaga actcttcctc acgcgcgtcg ggctcgacat
     cggcaaggtg
2581 tgggtcgcgg acgacggcgc cgcggtggcg gtctggacca cgccggagag
     cgtcgaagcg
2641 ggggcggtgt tcgccgagat cggcccgcgc atggccgagt tgagcggttc
     ccggctggcc
2701 gcgcagcaac agatggaagg cctcctggcg ccgcaccggc ccaaggagcc
     cgcgtggttc
2761 ctggccaccg tcggcgtctc gcccgaccac cagggcaagg gtctgggcag
     cgccgtcgtg
2821 ctccccggag tggaggcggc cgagcgcgcc ggggtgcccg ccttcctgga
     gacctccgcg
2881 ccccgcaacc tccccttcta cgagcggctc ggcttcaccg tcaccgccga
     cgtcgagtgc
2941 ccgaaggacc gcgcgacctg gtgcatgacc cgcaagcccg tgcctgagc
     ggccgcaatc
3001 tagaccaaac ttgtttattg cagcttataa tggttacaaa taaagcaata
     gcatcacaaa
3061 tttcacaaat aaagcatttt tttcactgca ttctagttgt ggtttgtcca
     aactcatcaa
3121 tgtatcttat catgtctgtg atcaggtacc aaagggcctc gtgatacgcc
     tatttttata
3181 ggttaatgtc atgataataa tggtttctta gacgtcaggt ggcacttttc
     ggggaaatgt
3241 gcgcggaacc cctatttgtt tatttttcta aatacattca aatatgtatc
     cgctcatgag
3301 acaataaccc tgataaatgc ttcaataata ttgaaaaagg aagagtatga
     gtattcaaca
3361 tttccgtgtc gcccttattc ccttttttgc ggcattttgc cttcctgttt
     ttgctcaccc
3421 agaaacgctg gtgaaagtaa aagatgctga agatcagttg ggtgcacgag
     tgggttacat
3481 cgaactggat ctcaacagcg gtaagatcct tgagagtttt cgccccgaag
     aacgttttcc
3541 aatgatgagc acttttaaag ttctgctatg tggcgcggta ttatcccgta
     ttgacgccgg
3601 gcaagagcaa ctcggtcgcc gcatacacta ttctcagaat gacttggttg
     agtactcacc
3661 agtcacagaa aagcatctta cggatggcat gacagtaaga gaattatgca
     gtgctgccat
3721 aaccatgagt gataacactg cggccaactt acttctgaca acgatcggag
     gaccgaagga
3781 gctaaccgct tttttgcaca acatggggga tcatgtaact cgccttgatc
     gttgggaacc
3841 ggagctgaat gaagccatac caaacgacga gcgtgacacc acgatgcctg
     tagcaatggc
3901 aacaacgttg cgcaaactat taactggcga actacttact ctagcttccc
     ggcaacaatt
```

| SEQUENCES |
|---|
| 3961 aatagactgg atggaggcgg ataaagttgc aggaccactt ctgcgctcgg<br>     cccttccggc |
| 4021 tggctggttt attgctgata aatctggagc cggtgagcgt gggtctcgcg<br>     gtatcattgc |
| 4081 agcactgggg ccagatggta agccctcccg tatcgtagtt atctacacga<br>     cggggagtca |
| 4141 ggcaactatg gatgaacgaa atagacagat cgctgagata ggtgcctcac<br>     tgattaagca |
| 4201 ttggtaactg tcagaccaag tttactcata tatactttag attgatttaa<br>     aacttcattt |
| 4261 ttaattaaaa agatctaggt gaagatcctt tttgataatc tcatgaccaa<br>     aatcccttaa |
| 4321 cgtgagtttt cgttccactg agcgtcagac cccgtagaaa agatcaaagg<br>     atcttcttga |
| 4381 gatcctttt ttctgcgcgt aatctgctgc ttgcaaacaa aaaaaccacc<br>     gctaccagcg |
| 4441 gtggtttgtt tgccggatca agagctacca actcttttc cgaaggtaac<br>     tggcttcagc |
| 4501 agagcgcaga taccaaatac tgttcttcta gtgtagccgt agttaggcca<br>     ccacttcaag |
| 4561 aactctgtag caccgcctac atacctcgct ctgctaatcc tgttaccagt<br>     ggctgctgcc |
| 4621 agtggcgata agtcgtgtct taccgggttg gactcaagac gatagttacc<br>     ggataaggcg |
| 4681 cagcggtcgg gctgaacggg gggttcgtgc acacagccca gcttggagcg<br>     aacgacctac |
| 4741 accgaactga gatacctaca gcgtgagcta tgagaaagcg ccacgcttcc<br>     cgaagggaga |
| 4801 aaggcggaca ggtatccggt aagcggcagg gtcggaacag gagagcgcac<br>     gagggagctt |
| 4861 ccagggggaa acgcctggta tctttatagt cctgtcgggt ttcgccacct<br>     ctgacttgag |
| 4921 cgtcgatttt tgtgatgctc gtcaggggg cggagcctat ggaaaaacgc<br>     cagcaacgcg |
| 4981 gcctttttac ggttcctggc cttttgctgg ccttttgctc acatgttctt<br>     tcctgcgtta |
| 5041 tcccctgatt ctgtggataa ccgtattacc gcctttgagt gagctgatac<br>     cgctcgccgc |
| 5101 agccgaacga ccgagcgcag cgagtcagtg agcgaggaag cggaagagcg<br>     cccaatacgc |
| 5161 aaaccgcctc tccccgcgcg ttggccgatt cattaatgca gctggcacga<br>     caggtttccc |
| 5221 gactggaaag cgggcagtga gcgcaacgca attaatgtga gttagctc |
| SEQ ID NO: 4-<br>   1 tcgaggatcc tgacccatcc tgggcctcaa cttactcatc ctgggaacgg<br>     gagacgattc |
|   61 acagaagaaa gcatgcaaga gcagcgtcca ggctgaaaga actttggcca<br>     cctggcactg |
|  121 agaactgaat tccataggct gtgagctcta gcaatgccct gtggactcag<br>     ttctggtgcc |
|  181 cggcagtgct acaacatcaa tgccaaggcc gtggggcagc tgatggtttg<br>     ggctcccaac |
|  241 ttcccagcca ggtgcttctg caggcccaca tcttgcccac tgggctagct<br>     cga |

What is claimed is:

1. A method of producing transiently expressed miRNA 146b containing mesenchymal stem cells, comprising the steps of:
   transfecting a cell population of mesenchymal stem cells capable of producing exosomes with one or more plasmids encoding miRNA 146b,
   harvesting cells from the cell population after transfection, and
   confirming the presence of the miRNA 146b microRNA in one or more of the harvested cells.

2. A method of treating a subject suffering from a glioma with modified exosomes, comprising the steps of:
   transfecting an exosome producing cell population with one or more plasmids encoding miR-146b microRNA,
   harvesting said exosomes from the cell population or media containing same after transfection,
   confirming the presence of the miR-146b microRNA in one or more of the harvested exosomes; and
   administering to the subject one or more of the harvested exosomes in a pharmaceutically effective amount to treat the subject with the glioma.

3. A method of treating a subject suffering from a glioma with modified cells, comprising the steps of:
- transfecting a cell population capable of producing exosomes with one or more plasmids encoding miR-146b microRNA,
- harvesting cells from the cell population after transfection,
- confirming the presence of the miR-146b microRNA in one or more of the harvested cells, and
- administering to the subject one or more of the harvested cells in a pharmaceutically effective amount to treat the subject with the glioma.

4. The method of claim 2, wherein the exosome producing cell population comprises multipotent mesenchymal stromal cells.

5. The method of claim 2, wherein the subject is a human.

6. The method of claim 3, wherein the cell population comprises multipotent mesenchymal stromal cells.

7. A method of treating a subject suffering from a gliosarcoma or a glioblastoma with modified exosomes, comprising the steps of:
- transfecting an exosome producing cell population with a plasmid encoding miR-146b,
- harvesting exosomes from the cell population or media containing same after transfection,
- confirming the presence of miR-146b in one or more of the harvested exosomes; and
- administering to the subject miR-146b-containing exosomes in a pharmaceutically effective amount to treat the subject with gliosarcoma or glioblastoma.

8. A method of treating a subject suffering from suffering from gliosarcoma or glioblastoma with modified cells, comprising the steps of:
- transfecting a cell population capable of producing exosomes with a plasmid encoding miR-146b,
- harvesting cells from the cell population after transfection,
- confirming the presence of miR-146b in one or more of the harvested cells, and
- administering to the subject one or more of the harvested cells in a pharmaceutically effective amount to treat the subject with respect to the gliosarcoma or glioblastoma.

9. The method of claim 7, wherein the cell population comprises multipotent mesenchymal stromal cells, and the subject is a human.

10. The method of claim 1, wherein the cell-derived membrane vesicles comprise exosomes.

11. The method of claim 1, wherein the cell population comprises multipotent mesenchymal stromal cells.

12. The method of claim 2, wherein the cell population comprises multipotent mesenchymal stromal cells.

13. The method of claim 3, wherein the cell population comprises multipotent mesenchymal stromal cells.

14. The method of claim 3, wherein the subject is a human.

15. The method of claim 2, wherein the exosomes are administered intratumorally.

16. The method of claim 7, wherein the exosomes are administered intratumorally.

17. The method of claim 3, wherein the cell population is derived from the subject.

18. The method of claim 8, wherein the cell population is derived from the subject.

19. The method of claim 2, wherein the cell population is derived from the subject.

20. The method of claim 7, wherein the cell population is derived from the subject.

* * * * *